(12) United States Patent
Ahn et al.

(10) Patent No.: US 8,163,240 B2
(45) Date of Patent: Apr. 24, 2012

(54) DETECTION DEVICE AND SYSTEM

(75) Inventors: Chang Geun Ahn, Daejeon (KR); Chan Woo Park, Daejeon (KR); Jong Heon Yang, Daejeon (KR); In Bok Baek, Cheongju (KR); Chil Seong Ah, Daejeon (KR); Han Young Yu, Daejeon (KR); An Soon Kim, Daejeon (KR); Tae Youb Kim, Seoul (KR); Moon Gyu Jang, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 75 days.

(21) Appl. No.: 12/682,545

(22) PCT Filed: Jun. 13, 2008

(86) PCT No.: PCT/KR2008/003329
§ 371 (c)(1),
(2), (4) Date: Apr. 9, 2010

(87) PCT Pub. No.: WO2009/075432
PCT Pub. Date: Jun. 18, 2009

(65) Prior Publication Data
US 2011/0194976 A1     Aug. 11, 2011

(30) Foreign Application Priority Data
Dec. 10, 2007   (KR) .................. 10-2007-0127816

(51) Int. Cl.
*G01N 15/06*   (2006.01)
*G01N 33/00*   (2006.01)
*G01N 33/48*   (2006.01)
*G01N 27/00*   (2006.01)

(52) U.S. Cl. ... 422/82.01; 422/50; 422/68.1; 422/82.02; 422/82.03; 436/43; 436/63; 436/149

(58) Field of Classification Search .................. 422/50, 422/68.1, 82.01, 82.02, 82.03; 436/43, 63, 436/149
See application file for complete search history.

(56) References Cited

U.S. PATENT DOCUMENTS
5,466,348 A * 11/1995 Holm-Kennedy ............ 205/775
(Continued)

FOREIGN PATENT DOCUMENTS
KR   1019910007083   4/1991
(Continued)

OTHER PUBLICATIONS

Massimo Barbaro et al., "Fully electronic DNA hybridization detection by a standard CMOS biochip," Sensors and Actuators B: Chemical, Oct. 25, 2006, pp. 41-46, vol. 118, Issues 1-2, 2006 Elsevier B.V.

(Continued)

*Primary Examiner* — Brian J Sines

(57) ABSTRACT

A detection device and system are provided. The detection device includes a detection capacitor and a Field Effect Transistor (FET). The detection capacitor has a reactive material layer reacting to a specific functional group in a fluid, and first and second electrodes disposed on the both surfaces of an insulating layer, and the FET has a source electrode connected with the second electrode, a gate electrode connected with the first electrode, and a drain electrode. Here, the insulating layer of the detection capacitor is thicker than a gate insulating layer of the FET.

7 Claims, 4 Drawing Sheets

U.S. PATENT DOCUMENTS

| | | | |
|---|---|---|---|
| 5,663,081 A | 9/1997 | Sung et al. | |
| 7,462,512 B2 * | 12/2008 | Levon et al. | 438/123 |
| 2002/0006632 A1 | 1/2002 | Ponnampalam et al. | |
| 2005/0230271 A1 * | 10/2005 | Levon et al. | 205/789 |
| 2005/0263410 A1 | 12/2005 | Hsiung | |

FOREIGN PATENT DOCUMENTS

| | | |
|---|---|---|
| KR | 1019930014765 | 7/1993 |
| KR | 100148598 B1 | 5/1998 |
| KR | 100211947 B1 | 5/1999 |

OTHER PUBLICATIONS

Ariel Cohen et al., "Depletion type floating gate p-channel MOS transistor for recording action potentials generated by cultured neurons," Biosensors and Bioelectronics, Jul. 15, 2004, pp. 1703-1709, vol. 19, Issue 12, 2004 Elsevier B.V.

International Search Report for PCT/KR2008/003329 filed on Jun. 13, 2008.

* cited by examiner

[Fig. 1]
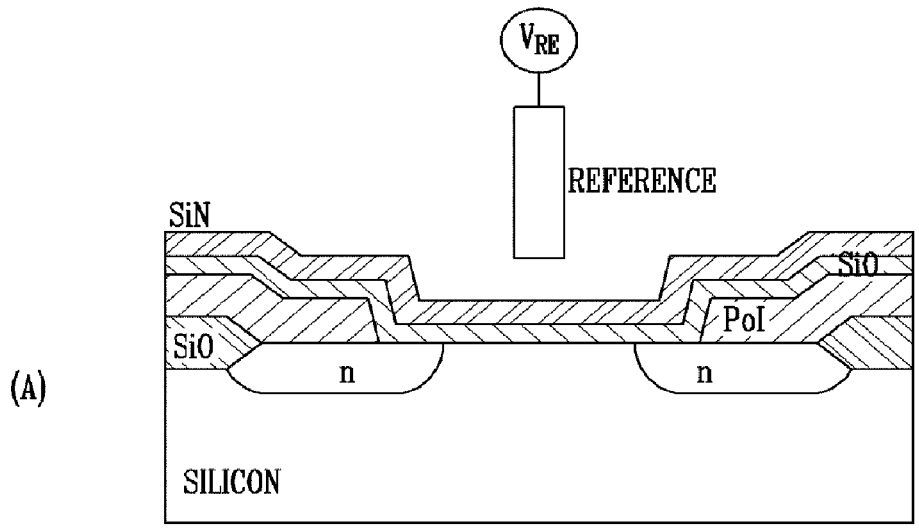
(A)
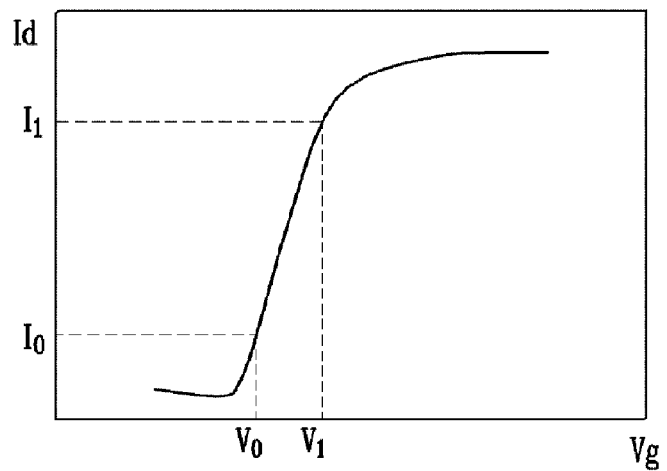
(B)
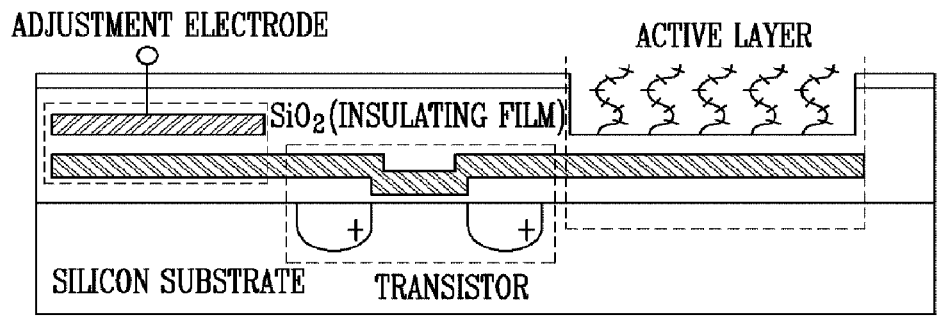
(C)

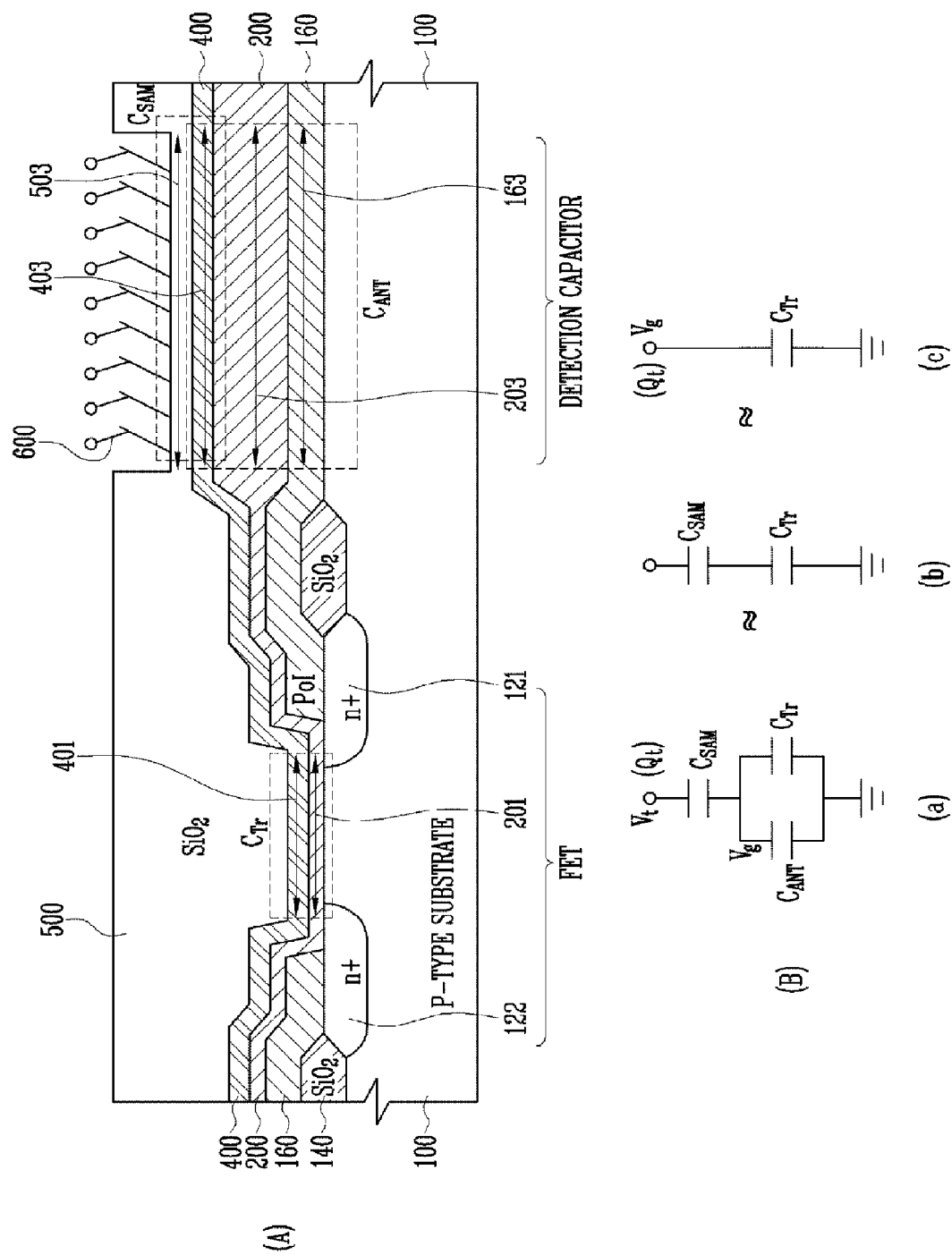
[Fig. 2]

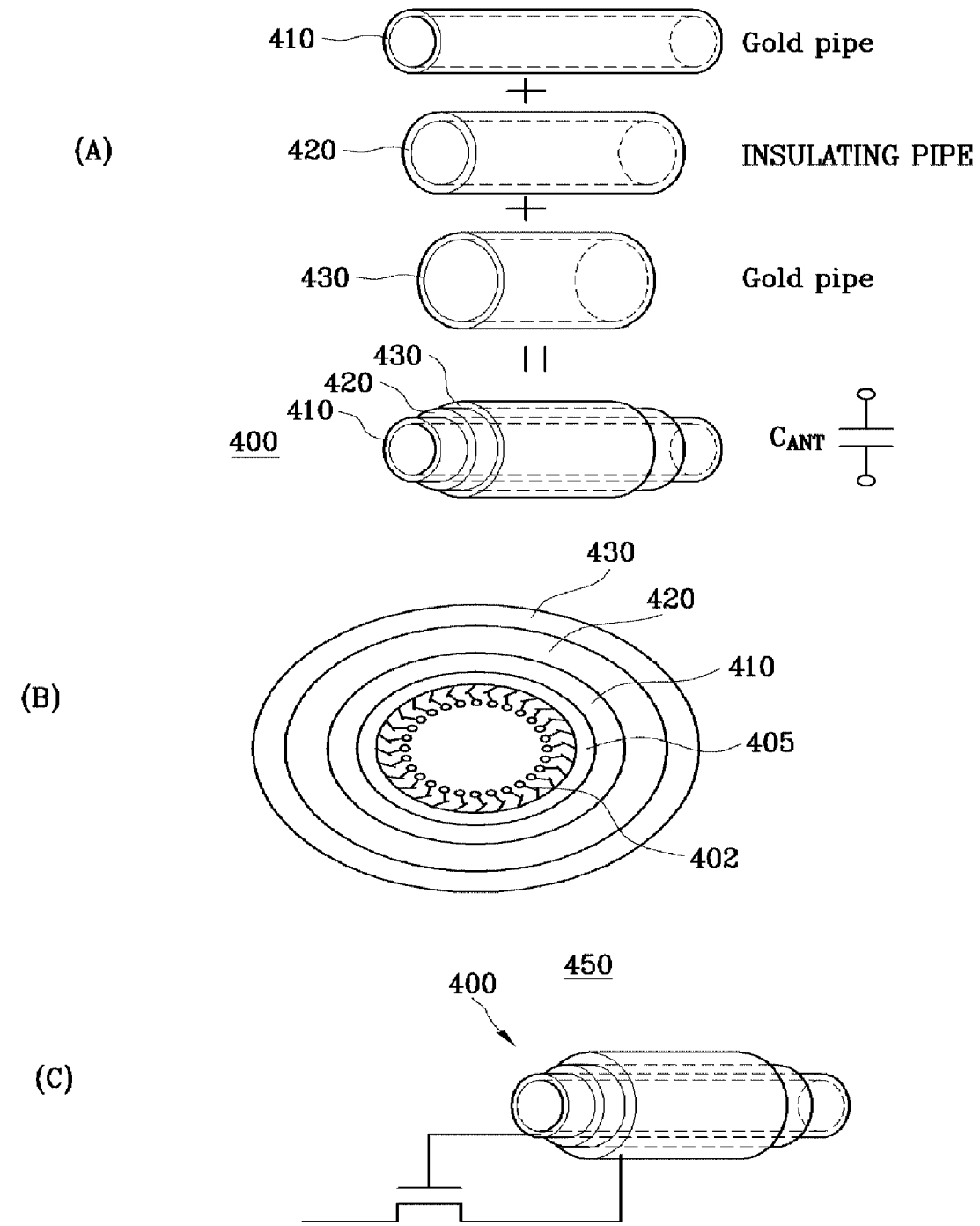

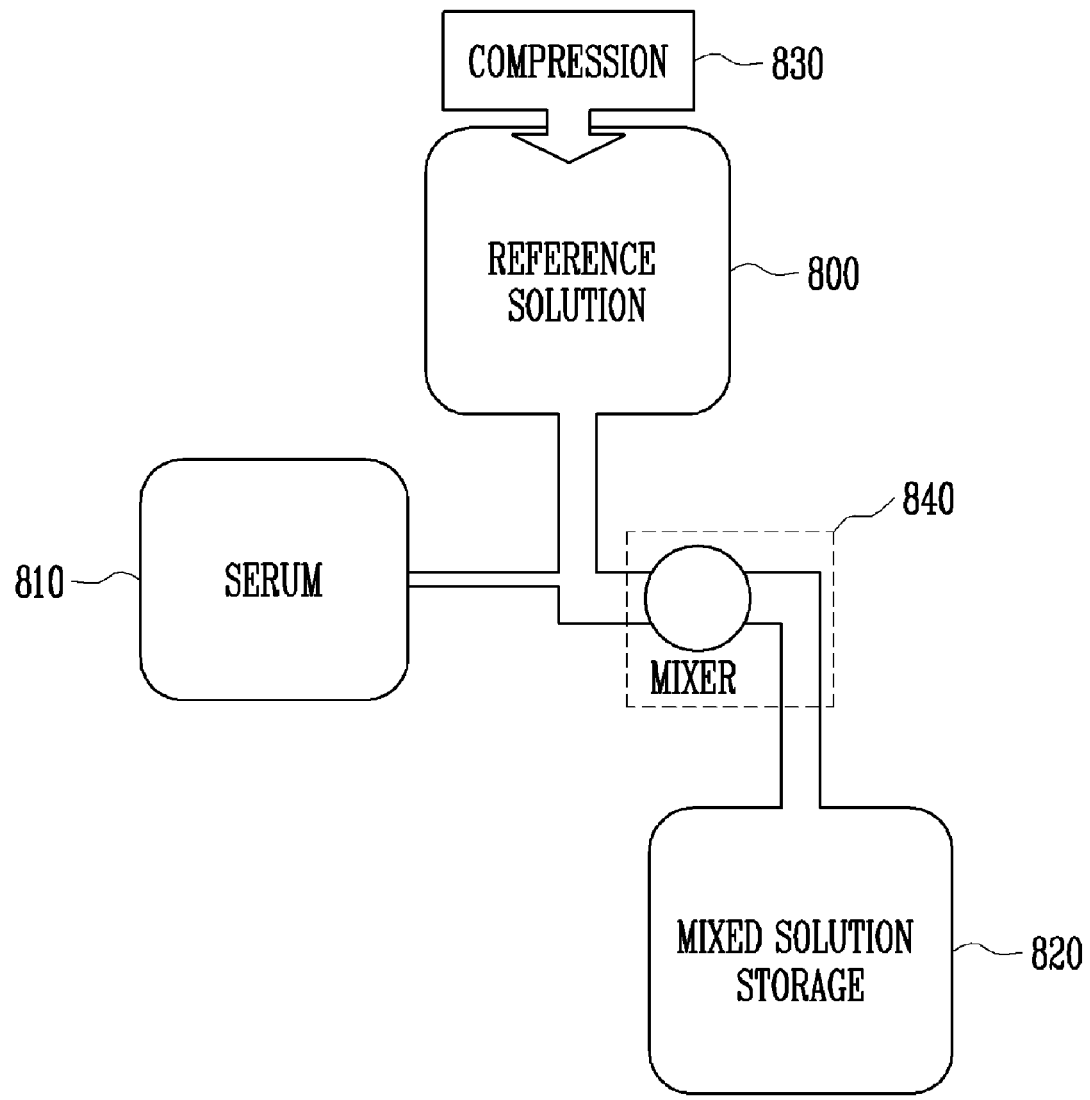
[Fig. 4]

DETECTION DEVICE AND SYSTEM

TECHNICAL FIELD

The present invention relates to a detection device for detecting a specific functional group existing in a fluid, and more particularly, to a detection device that is a biosensor for detecting biomolecules having a specific functional group, can be fabricated by applying a semiconductor fabrication process and a detection system having the detection device.

The present invention is derived from research supported by the IT R&D program of the Ministry of Information and Communication and the Institute for Information Technology Advancement (MIC/ITA) in Korea (project title: Ubiquitous Health Monitoring Module and System Development).

BACKGROUND ART

A detection device for detecting a specific functional group existing in a fluid is expected to be widely used in the field of biosensors detecting amino acids or DNA molecules in a body fluid.

Lately, Information Technology (IT) and Nanotechnology (NT), which have hitherto been separately improved, have been fused together, thereby rapidly developing a new technological base on the basis of Biology Technology (BT). In particular, research on a biosensor for detecting protein in blood is actively being conducted in the field of nano-biochip which is one of NT-BT fusion technologies.

In the field of nano-biochip, various methods for detecting, analyzing and quantifying a specific biomaterial are being developed. A representative one of the methods detects a specific biomaterial by fluorescence labeling. The fluorescence labeling method is frequently employed in currently used DNA chips.

However, the fluorescence labeling method requires an additional step of bio-chemically preparing a sample for measurement such as blood and saliva to detect a specific biomaterial, and thus it is difficult to apply various materials to the method. For example, when protein is labeled, about 50% of functional protein is inactivated in an unspecific labeling process. Therefore, only a very small amount of analyte can be appropriately used for a purpose.

For this reason, biosensors have begun to be proposed which have improved sensitivity and reproducibility and can be mass-produced through a semiconductor process. As an example, a high-sensitivity biosensor capable of detecting a specific material using a Si-nanowire fabricated through Chemical Vapor Deposition (CVD) has been widely researched according to a bottom-up method for several recent years. However, lately, a Si-nanowire biosensor which can be mass-produced in a top-down method using a current industrial Complementary Metal-Oxide Semiconductor (CMOS), easily implemented and has ensured reproducibility is being widely researched. In addition, many research results on an Ion-Sensitive Field Effect Transistor (ISFET) that is fabricated using a CMOS process as is and has the same structure as an FET, have been reported.

An ISFET is similar to a nanowire biosensor in that target molecules in solution react with probe molecules of a sensor to increase surface charges and thereby conductivity of the sensor is changed. On the other hand, an ISFET has a characteristic structure of a general FET, a gate voltage is determined by target molecules adsorbed on the upper part of a gate, and the gate voltage follows a pattern of an operation characteristic curve of the ISFET.

However, a changed amount of charge caused by a reaction between probe molecules and target molecules cannot remarkably change the total gate voltage, and thus the sensitivity of the ISFET considerably deteriorates. Since pH concentration and salinity of human blood directly affecting the amount of charge of target molecules vary according to persons, it is preferable to dilute blood with much reference solution. Therefore, to remove dependence on conditions of serum, the serum must be diluted with reference solution, and thus a high-sensitivity sensor may be further required.

In addition, it is not easy to dilute blood extracted from human body with reference solution after quantifying a small amount of blood. When a dilution ratio is one over several hundreds of thousands, an extremely small amount of blood must be quantified and diluted with reference solution, or blood must be diluted with a very large amount of reference solution. This is an unrealistic and very difficult technical problem.

DISCLOSURE OF INVENTION

Technical Problem

The present invention is directed to providing a detection device having improved sensitivity.

The present invention is also directed to providing a detection system having a structure automatically diluting serum with reference solution and capable of preferably employing a detection device of the present invention. In other words, a detection system is provided as a synthetic biosensing system employing a system for automatically diluting serum with reference solution and a detection device having improved sensitivity.

Technical Solution

One aspect of the present invention provides a detection device, comprising a detection capacitor and a Field Effect Transistor (FET). The detection capacitor has a reactive material layer reacting to a specific functional group in a fluid, and first and second electrodes disposed on both surfaces of an insulating layer, and the FET has a source electrode connected with the second electrode, a gate electrode connected with the first electrode, and a drain electrode. Here, the insulating layer of the detection capacitor is thicker than a gate insulating layer of the FET.

Another aspect of the present invention provides a detection system, comprising: a serum storage for storing a serum fluid to be a detection object; a solvent storage for storing a solvent for diluting the serum fluid to an appropriate concentration for detection; a mixing pipe for mixing the serum fluid flowing out of the serum storage with the solvent flowing out of the solvent storage therein; and a detection device for detecting a specific functional group included in the fluid mixed in the mixing pipe.

Advantageous Effects

A detection device and detection system according to the present invention can be fabricated at low cost while having improved detection performance.

More specifically, the detection device of the present invention uses an electrical characteristic of a subthreshold region of a transistor, has a large charge integrator, and thereby maximizes the amount of change in voltage applied to the gate of the transistor using a capacitor-share effect and a charge transfer technique, thus having much higher sensitivity than a conventional detection device.

In addition, the present invention can immediately detect a specific functional group while diluting serum with reference solution at a fixed concentration.

Furthermore, a detection device according to the present invention has high durability and is easily fabricated, applied, and replaced because its capacitor can be fabricated in the form of a tube.

BRIEF DESCRIPTION OF THE DRAWINGS

FIG. 1A is a cross-sectional view for describing an operating principle of a general Ion-Sensitive Field Effect Transistor (ISFET) detection device.

FIG. 1B is graph showing a characteristic curve of a Metal-Oxide-Semiconductor Field Effect Transistor (MOSFET) describing an operation characteristic of an ISFET.

FIG. 1C is a cross-sectional view of an ISFET detection device having an adjustment electrode.

FIG. 2A is a cross-sectional view of a structure of a detection device according to an exemplary embodiment of the present invention.

FIG. 2B shows equivalent circuits according to an electrical characteristic of the biosensor of FIG. 2A.

FIG. 3A is a conceptual diagram showing a structure of a pipe-type detection capacitor of a detection device according to another exemplary embodiment of the present invention.

FIG. 3B is a cross-sectional view of the pipe-type detection capacitor of FIG. 3A.

FIG. 3C illustrates a circuit connection between the pipe-type detection capacitor of FIG. 3A and an FET.

FIG. 4 is a block diagram of a detection system according to an exemplary embodiment of the present invention.

MODE FOR THE INVENTION

A technique has been proposed, of separately forming a charge integrator at a part where charge can be integrated in the structure of an Ion-Sensitive Field Effect Transistor (IS-FET), transferring the integrated charge to a gate to maximize a changed amount of charge caused by a reaction between probe molecules and target molecules, and thereby fabricating a biosensor having a sensitive structure for detecting a specific biomaterial.

FIG. 1A is a cross-sectional view for describing an operating principle of an ISFET sensor shown as a device for detecting a body fluid, and FIG. 1B is a characteristic curve of a Metal-Oxide-Semiconductor Field Effect Transistor (MOSFET) illustrating an operation characteristic of an ISFET.

As illustrated in FIG. 1A, the ISFET sensor has the structure of a general MOSFET device having a drain and a source. However, there is no gate capable of controlling a channel through which current flows between the source and the drain. When probe molecules (not shown in the drawings) reacting to a specific functional group of a body fluid are fixed in the upper part of the channel, they react to target molecules including the specific functional group, control power of the gate is changed by a change in the amount of charge of the target molecules, and thus the current between the source and the drain is changed.

As illustrated in FIG. 1B, drain current of a fabricated device having an MOSFET structure is very sensitively changed according to gate voltage in a subthreshold region. If drain current that can flow when initial gate voltage is Va is Ia, drain current becomes Ib when target molecules are combined with probe molecules formed on the surface of a gate and change gate voltage to be Vb.

Therefore, when the subthreshold region is used as a sensing region, it is possible to increase a change in sensing current by changing a small amount of gate voltage. However, since the amount of change in gate voltage that can be caused by surface reaction per unit area is very small, the amount of change in drain current, which is a sensing signal according to the gate voltage, is not so large. In other words, the sensitivity of the sensor is not satisfactory.

FIG. 1C is a cross-sectional view of an ISFET sensor having an adjustment electrode.

As illustrated in FIG. 1C, unlike the general ISFET shown in FIG. 1A, the ISFET sensor does not have a reference electrode for generating reference voltage but has an adjustment electrode capable of performing such a function. In addition, the ISFET sensor additionally has a charge integrator instead of exposing an upper channel part, i.e., the upper surface of a gate. Since the ISFET sensor has the charge integrator having a large area to detect target material without using the upper channel part having a small area, more uniform results can be obtained. However, as the amount of charge is increased by enlarging the area of the charge integrator, the capacitance increases as much as the enlarged amount of the area. Thus, the amount of change in gate voltage is fixed regardless of a change in area.

Hereinafter, exemplary embodiments of the present invention will be described in detail. However, the present invention is not limited to the exemplary embodiments disclosed below, but can be implemented in various types. Therefore, the present exemplary embodiments are provided for complete disclosure of the present invention and to fully inform the scope of the present invention to those ordinarily skilled in the art. In the drawings, the size and relative sizes of layers and regions may be exaggerated for clarity. It will be understood that when a layer is referred to as being "on" another layer or a substrate, it can be directly on the other layer or the substrate, or still another layer may be interposed between them. Throughout the drawings, like reference numerals denote like elements.

In addition, a method of fabricating a biodevice or already-known one of technologies related to the method is not described below. This means that the present invention is not limited by the already-known technology.

Meanwhile, a source and drain of a general MOS transistor are relatively distinguished from each other except for a case in which the source and drain are fabricated to have asymmetric characteristics. Therefore, the terms "source" and "drain" are used for convenience only in the present invention.

Exemplary Embodiments

FIG. 2A is a cross-sectional view of a structure of a detection device according to this exemplary embodiment of the present invention, and FIG. 2B shows equivalent circuits for describing an operating principle of the biosensor of FIG. 2A according to an electrical characteristic. For the purpose of description, the illustrated detection device may be roughly divided into a detection capacitor and an FET.

The detection capacitor includes a reactive material layer 600 and a capacitor structure. The reactive material layer 600 includes probe molecules reacting to a specific functional group in a fluid. The capacitor structure includes a polysilicon film 163 as a second electrode formed under the reactive material layer 600 in contact with a lower surface of a $SiO_2$ layer 203 functioning as a capacitor insulating layer, and a metal film 403 as a first electrode in contact with an upper surface of the $SiO_2$ layer 203. In addition, the detection capacitor may further include a link material layer 503 as a surface insulating layer functioning as a capacitor between the reactive material layer 600 and the metal film 403 that is the first electrode.

A polysilicon layer 160 including the polysilicon film 163 as the second electrode and a metal layer 400 including the metal film 403 as the first electrode may be made of a conductive material having a higher conductivity than a p-type substrate 100 that is a substrate of the transistor.

The polysilicon film 163 that is the second electrode of the detection capacitor may be omitted according to embodiments. However, when the polysilicon film 163 exists, a performance of transferring a characteristic of the detection capacitor changed by a specific functional group included in a serum fluid to the FET improves.

When there is no additional electrode between the substrate and the detection capacitor insulating layer, an interface between the substrate and the detection capacitor insulating layer serves as a capacitor electrode. In this case, the second electrode of the detection capacitor and the substrate of the FET are shared between the detection capacitor and the FET, which deteriorates flexibility for adjusting a bias to the detection capacitor and the FET. In addition, in this case, an additional process for setting as ground the substrate on which the second electrode of the detection capacitor is formed is required. Furthermore, a bias may be applied to the interface between the substrate and the detection capacitor insulating layer due to a characteristic of the interface. Due to the bias, depletion occurs in a region of the substrate as bulk silicon having a low doping concentration near the second electrode, and thus the capacitor unnecessarily varies.

Therefore, the second electrode may be formed of a material, e.g., metal or polysilicon, having a higher conductivity than the p-type substrate that is the substrate of the FET separately from the substrate.

As the FET, a transistor structure is formed to have a source electrode 121 connected with the polysilicon film 163, a gate electrode 401, and a drain electrode 122. As a part of the metal layer 400, the gate electrode 401 is formed of the same material as the metal film 403 of the detection capacitor through the same process as the metal film 403 so as to be connected with the first electrode of the detection capacitor. To enhance another characteristic, the gate electrode 401 may be formed of another material through another process separately from the metal film 403.

In FIG. 2A, the $SiO_2$ layer 203 that is the insulating layer of the detection capacitor is formed to be connected with an insulating layer 201 at the lower part of the gate electrode 401 of the FET. However, it can be seen that the thickness of the part functioning as the insulating layer 203 of the detection capacitor is remarkably larger than that of the part functioning as the gate insulating layer 201 of the transistor. This is for reducing the capacitance of the detection capacitor according to the spirit of the present invention. The very thick insulating layer causes a remarkable change in the operation characteristic of the device.

Although the insulating layer 201 at the lower part of the gate electrode 401 and the insulating layer 203 of the detection capacitor are implemented as one body, they are generally formed through different processes. For example, while $SiO_2$ or a high-k material is used for a gate electrode insulating layer, a low-k material is used as an insulating layer of the capacitor to obtain small enough capacitance from a thin thickness.

As illustrated in FIG. 2B, the structure of FIG. 2A can be expressed by an electrical equivalent circuit of (a). Here, when the area of the detection capacitor that is a charge integrator is enlarged, a capacitance $C_{ANT}$ increases. On the other hand, when the insulating layer 203 of the detection capacitor thickens, the capacitance $C_{ANT}$ decreases. When the capacitance $C_{ANT}$ is reduced to be a fifth of a capacitance $C_{Tr}$ or less using the characteristic, the structure can be simply expressed by an equivalent circuit of (b). When the capacitance $C_{ANT}$ is adjusted to be one fifth of a capacitance $C_{Tr}$ or less by thickening the insulating layer 203 as much as the increased area of the active layer of the detection capacitor, it is possible to minimize the influence of the capacitance $C_{ANT}$.

The capacitances $C_{ANT}$ and $C_{Tr}$ are determined according to an area $A_{ANT}$ of the detection capacitor, a channel area $A_{gate}$ of the transistor, a thickness $t_{ANT}$ and a permittivity $\in_{ANT}$ of the capacitor insulating layer, and a thickness $t_{ox}$ and a permittivity $\in_{OX}$ of the transistor insulating layer. Thus, the parameters must satisfy the relationship of an inequality below. This is because a capacitance difference of five times allows influence of one capacitor to be ignored.

$$5C_{ANT} \leq C_{Tr} \Leftrightarrow 5\in_{ANT}A_{ANT}/t_{ANT} \leq \in_{OX}A_{gate}/t_{OX} \quad \text{[Inequality 1]}$$

In addition, the surface area of the reactive material layer of the detection capacitor is much larger than the area of the gate 401 of the transistor, and the height of the link material layer 503 constituting a capacitor $C_{SAM}$ is generally smaller than that of a gate oxide layer. Therefore, the equivalent circuit of (b) can be simply changed into an equivalent circuit of (c). The equivalent circuit of (c) denotes that an entire equivalent capacitance is fixed at $C_{Tr}$, and thus it is possible to increase a changed amount of charge and simultaneously and remarkably increase a changed amount of voltage by causing more reactions of a target material using a wide charge integrator.

According to implementations, the detection device of this exemplary embodiment may have a plurality of the detection capacitors or a plurality of the structures of FIG. 2A including the detection capacitor and the FET. In this case, reactive material layers in which different probe molecules are fixed may be formed on surfaces of the respective capacitors.

Meanwhile, the probe molecules constituting the reactive material layer of this exemplary embodiment may be one selected from the group of an antigen, an antibody, DNA and protein, or a combination thereof.

FIGS. 3A to 3C illustrate a structure of a detection device in which a detection capacitor is implemented in the form of a pipe according to another exemplary embodiment. Like the detection device of FIG. 2A, the detection device of this exemplary embodiment also may be roughly divided into an FET and a detection capacitor for charge integration.

The FET of the illustrated detection device has a completely packaged common transistor installed in a reader and thus can constitute a low-priced and reproducible structure. In addition, a part of a pipe through which a serum fluid passes can be implemented as a detection capacitor. More specifically, in the pipe-type detection capacitor of this exemplary embodiment, an insulating pipe 420 made of insulating material or dielectric material is an insulating layer of the capacitor, and two conductive pipes 410 and 430 bonded to the inner surface and the outer surface of the pipe 420 are first and second electrodes of the capacitor. The conductive pipes 410 and 430 may be easily implemented by metal pipes, and the insulating pipe 420 may be implemented at low cost using high-polymer synthetic resin.

On the inner conductive pipe 410 corresponding to the first electrode, a specific material, e.g., Au, that can facilitate surface fixation of probe molecules constituting a reactive material layer may be coated, or the metal pipe itself may be formed of a material on which the probe molecules can be fixed. Therefore, according to this exemplary embodiment, a reactive material layer 402 reacting to a specific functional group in a serum fluid may be formed in direct contact with the inner conductive pipe 410 or in contact with a surface fixable material layer 405 coated on the inside of the inner conductive pipe 410.

The insulating pipe 420 is interposed between the inner conductive pipe 410 and the outer conductive pipe 430 of this exemplary embodiment, thereby forming a capacitor structure. Here, the sizes, diameters or shapes of the pipes may be different to control sensitivity and an analyzable region. In addition, the inner and outer conductive pipes 410 and 420 must not be conductively connected with each other and may be designed to easily get contact with an external electrode.

A detection process of the detection devices shown in FIGS. 2A to 3C is as follows. As described above, detection of target molecules including a specific functional group based on probe molecule reaction in a reactive material layer causes a change in the amount of charge in a detection capacitor, and is transferred as a changed amount of gate voltage of an FET whose gate and source are connected with first and second electrodes of the detection capacitor. The changes caused by target molecule detection are read by a reader from a changed amount of drain current, and the read data can be analyzed in various ways and displayed as a detection result.

In order to detect target molecules, the electrical characteristic of a subthreshold region, a current of which is sensitively changed according to a change in the voltage of the FET in the transistor, must be used. Therefore, a change in gate voltage caused by reaction of the reactive material layer must be achieved in the subthreshold region of the FET according to details of the detection capacitor and the FET, an external bias, and so on.

FIG. 4 is a block diagram of a detection system automatically diluting a serum fluid with a solvent solution at a specific ratio and thereby attempting detection according to an exemplary embodiment of the present invention.

The illustrated detection system includes a serum storage 810 storing a serum fluid to be a detection object, a solvent storage 800 storing a solvent for diluting the serum fluid to an appropriate concentration for detection, a mixing pipe 840 in which the serum fluid flowing out of the serum storage 810 is mixed with the solvent flowing out of the solvent storage 800, and a detection device (not shown) for detecting a specific functional group included in the fluid mixed in the mixing pipe 840.

As illustrated in FIG. 4, together with the storages 800 and 810 for reference solution and serum, a compressor 830 as a means for discharging solution applying pressure to the reference solution to move the serum fluid stored in the solution storage 800 to the mixing pipe 840 may be further included. As a mixed solution processor for processing mixed solution used for detection, a mixed solution storage 820 storing mixed solution may be further included. According to implementations, a decompressor for actively inhaling mixed solution to the mixed solution storage 820 may be included.

In the drawing, the detection system is implemented such that the serum fluid stored in the serum storage 810 is moved to the mixed pipe 840 due to the Bernoulli pressure of flowing reference solution. However, the detection system may further include a serum discharging means for moving the serum fluid stored in the serum storage 810 to the mixed pipe 840.

A detection process using the detection system is as follows. First, serum, e.g., blood or urine, is injected into the serum storage 810. When pressure is applied to the storage 800 for a solvent, i.e., reference solution, the solvent flows out, and the serum flows out from the serum storage 810 due to a difference in pressure. The solvent is mixed with the serum in the mixing pipe 840. Here, a dilution ratio is determined according to a ratio of the cross-sectional area of a solvent outlet pipe to the cross-sectional area of a serum outlet pipe. In addition, an additional mixer connected with the mixing pipe 840 may be further included in order to more efficiently mix the flowing serum with the flowing solvent.

Besides the compressor 830 of FIG. 4, a compressor or decompressor may be installed according to some combinations. The compressor or decompressor may apply pressure by simply pushing, injecting gas, and injecting the same liquid. The mixer may be various types of general mixers.

A detection device according to the present invention, in particular, the detection device of FIG. 3A may be installed in the detection system of FIG. 4. Since the detection device of FIG. 3A has an insulating layer of a detection capacitor having the form of a pipe, i.e., an insulating pipe, the insulating pipe of the detection capacitor may be implemented to be a part or the whole of the mixing pipe of the detection system shown in FIG. 4. This implementation can maximize detection efficiency while reducing manufacturing cost.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A detection device, comprising:
   a detection capacitor including a reactive material layer reacting to a specific functional group in a fluid, and first and second electrodes disposed on both surfaces of an insulating layer; and
   a Field Effect Transistor (FET) including a source electrode connected with the second electrode, a gate electrode connected with the first electrode, and a drain electrode,
   wherein the insulating layer of the detection capacitor is thicker than a gate insulating layer of the FET.

2. The detection device of claim 1, wherein the second electrode is formed of a material having a higher conductivity than a substrate of the FET.

3. The detection device of claim 2, wherein the first electrode is formed of the same material as the gate electrode.

4. The detection device of claim 1, wherein a capacitance between the first electrode and the second electrode is smaller than one fifth of a gate capacitance of the FET.

5. The detection device of claim 1, wherein the detection capacitor includes a link material layer between the first electrode and the reactive material layer.

6. The detection device of claim 1, wherein the insulating layer of the detection capacitor has the form of a pipe through which the fluid for detection is moved, the first electrode has the form of a pipe in contact with an inner surface of the insulating layer, the second electrode has the form of a pipe in contact with an outer surface of the insulating layer, and the reactive material layer is disposed inside the first electrode.

7. The detection device of claim 6, wherein the insulating layer of the detection capacitor is made of high-polymer synthetic resin, and the first and second electrodes are made of metal.

* * * * *